United States Patent
Takeshita et al.

(10) Patent No.: US 9,242,909 B2
(45) Date of Patent: Jan. 26, 2016

(54) METHOD FOR REFINING DICYCLOPENTADIENE

(75) Inventors: Takaaki Takeshita, Tokyo (JP); Takeshi Omata, Pasadena, TX (US); Takashi Suzuki, Tokyo (JP); Takashi Morikita, Tokyo (JP); Satoshi Mori, Tokyo (JP)

(73) Assignees: JX NIPPON OIL & ENERGY CORPORATION, Tokyo (JP); JX NIPPON CHEMICAL TEXAS INC., Pasadena, TX (US)

(*) Notice: Subject to any disclaimer, the term of this patent is extended or adjusted under 35 U.S.C. 154(b) by 967 days.

(21) Appl. No.: 13/141,145

(22) PCT Filed: Nov. 11, 2009

(86) PCT No.: PCT/JP2009/069210
§ 371 (c)(1),
(2), (4) Date: Jul. 26, 2011

(87) PCT Pub. No.: WO2010/073841
PCT Pub. Date: Jul. 1, 2010

(65) Prior Publication Data
US 2011/0272268 A1 Nov. 10, 2011

(30) Foreign Application Priority Data

Dec. 26, 2008 (JP) ................................ 2008-333241
Dec. 26, 2008 (JP) ................................ 2008-333399

(51) Int. Cl.
*C07C 7/04* (2006.01)
*C10G 50/00* (2006.01)
(Continued)

(52) U.S. Cl.
CPC . *C07C 7/04* (2013.01); *C10G 50/00* (2013.01); *C10G 55/04* (2013.01); *C07C 2103/68* (2013.01); *C10G 2300/104* (2013.01)

(58) Field of Classification Search
CPC .......... C07C 7/04; C07C 13/16; C07C 7/005; C10G 50/00
See application file for complete search history.

(56) References Cited

U.S. PATENT DOCUMENTS 3,676,509 A 7/1972 Heiman
4,246,367 A * 1/1981 Curtis, Jr. ................ 525/49
(Continued)

FOREIGN PATENT DOCUMENTS

JP 57-064622 4/1982
JP 62010025 1/1987
(Continued)

OTHER PUBLICATIONS

International Preliminary Report on Patentability for PCT/JP2009/069210, mail date is Aug. 25, 2011.
(Continued)

*Primary Examiner* — Tam M Nguyen
(74) *Attorney, Agent, or Firm* — Greenblum & Bernstein, P.L.C.

(57) ABSTRACT

A first method for refining dicyclopentadiene of the present invention is characterized in that the method separates and recovers dicyclopentadiene by distilling the crude dicyclopentadiene that contains dicyclopentadiene and is obtained by removing a C5 fraction and a BTX fraction from the reaction product obtained by dimerization reaction of the cracked gasoline by-produced in an ethylene plant that uses as feed stock a C2 fraction, a C3 fraction and a C4 fraction. A second method for refining dicyclopentadiene of the present invention is characterized in that the dicyclopentadiene-containing fraction refined by distillation is brought into contact with an inert gas or a hydrocarbon gas having 1 to 3 carbon atoms.

11 Claims, 4 Drawing Sheets

(51) Int. Cl.
*C07C 13/16* (2006.01)
*C10G 55/04* (2006.01)

(56) References Cited

U.S. PATENT DOCUMENTS

| | | | |
|---|---|---|---|
| 4,946,582 A * | 8/1990 | Torihata et al. | 208/251 R |
| 5,254,781 A | 10/1993 | Calamur et al. | |
| 5,321,177 A | 6/1994 | Nakamura et al. | |
| 6,420,621 B2 | 7/2002 | Sha et al. | |
| 2001/0056216 A1 | 12/2001 | Sha et al. | |
| 2003/0100809 A1 | 5/2003 | Tian et al. | |
| 2003/0149322 A1 | 8/2003 | Koss et al. | |
| 2004/0158113 A1 * | 8/2004 | Srinivas et al. | 585/721 |
| 2009/0112033 A1 | 4/2009 | Hosotani | |

FOREIGN PATENT DOCUMENTS

| | | |
|---|---|---|
| JP | 62010025 A * | 1/1987 |
| JP | 63-174939 | 7/1988 |
| JP | 3240740 | 10/1991 |
| JP | 3240741 | 10/1991 |
| JP | 5-78263 | 3/1993 |
| JP | 6-506482 | 7/1994 |
| JP | 7-39354 | 5/1995 |
| JP | 11-193250 | 7/1999 |
| JP | 2003-183188 | 7/2003 |
| JP | 2003-525971 | 9/2003 |
| WO | 2007/129736 | 11/2007 |

OTHER PUBLICATIONS

International Search Report for PCT/JP2009/069210, mail date is Jan. 26, 2010.

"Petrochemistry Process", Editor: The Japan Petroleum Institute, Publisher: Sawako Noma, Publishing Office: Office: Kodansha Ltd., Aug. 10, 2001, pp. 21-30; and a partial English language translation thereof.

Office Action for JP Application No. 2008-333241, mailed on May 7, 2013.

* cited by examiner

METHOD FOR REFINING DICYCLOPENTADIENE

TECHNICAL FIELD

The present invention relates to a method for refining dicyclopentadiene.

BACKGROUND ART

Dicyclopentadiene (DCPD), which is represented by the following structural formula, is widely used as a starting material for the production of compounds such as ethylidene norbornene and cycloolefin polymer, and refined high-purity DCPD is needed depending on the intended application as the case may be.

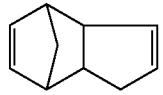

[Formula 1]

Dicyclopentadiene (DCPD)

Industrially, DCPD is produced by dimerizing cyclopentadiene contained in the C5 fraction of the pyrolysis product of naphtha. In this case, a step of separating the C5 fraction from the pyrolysis product, and facilities specialized for use for dimerizing the C5 fraction and others are needed.

As another method, for example, Patent Literature 1 U.S. Pat. No. 3,676,509 proposes a method for producing dicyclopentadiene in which method the C8 and higher fractions from a LPG cracking unit are pyrolyzed, and the high-purity cyclopentadiene obtained from the decomposition products is dimerized to yield dicyclopentadiene.

Additionally, as another method for producing high-purity DCPD, for example, Patent Literature 2 proposes a method in which cyclopentadiene contained in the C5 fraction obtained by pyrolysis of naphtha is dimerized into dicyclopentadiene, and thereafter, the dicyclopentadiene thus obtained is subjected to repeated distillations with a plurality of distillation towers.

CITATION LIST

Patent Literature

Patent Literature 1: U.S. Pat. No. 3,676,509
Patent Literature 2: Japanese Patent Publication No. 7-39354

SUMMARY OF INVENTION

Technical Problem

However, the methods described in U.S. Pat. No. 3,676,509 and Japanese Patent Publication No. 7-39354 both require a huge equipment investment and a huge operation cost for the purpose of performing the pyrolysis and the dimerization. On the other hand, when high-purity DCPD is used, a satisfactory hue as well as a satisfactory purity is generally required. In consideration of the economic efficiency in the production of dicyclopentadiene, it is desirable that the number of the distillation steps is small; however, no examples of the investigation of the methods for improving the hue in such a case have ever been found.

Solution to Problem

The present invention has been achieved under the above-described circumstances, and an object of the present invention is to provide a method for refining dicyclopentadiene which method enables to obtain high-purity dicyclopentadiene and is more advantageous than conventional methods from the aspects of the equipment cost and the operation cost. Another object of the present invention is to provide a method for refining dicyclopentadiene which method is capable of improving the hue of the dicyclopentadiene-containing fraction refined by distillation.

The present inventors have discovered that high-purity dicyclopentadiene can be separated and recovered by distillation from the specific crude dicyclopentadiene derived from the reaction product obtained by dimerization reaction of a cracked gasoline. Moreover, while investigating a method for obtaining high-purity dicyclopentadiene by a single distillation from the dicyclopentadiene-containing distillation object, the present inventors discovered that the color can be removed by bringing a specific gas into contact with the colored fraction separated by distillation from the top section of the distillation tower, and consequently dicyclopentadiene excellent in hue can be obtained. Additionally, the present inventors have perfected the present invention on the basis of these findings.

Specifically, the present invention provides a first method for refining dicyclopentadiene which method separates and recovers dicyclopentadiene by distilling the crude dicyclopentadiene that contains dicyclopentadiene and is obtained by removing a C5 fraction and a BTX fraction from the reaction product obtained by dimerization reaction of the cracked gasoline by-produced in an ethylene plant that uses as feed stock a C2 fraction, a C3 fraction and a C4 fraction.

It is to be noted that in the present specification, a cracked gasoline means the C5 to C9 fractions as the by-products obtained from an ethylene cracker and additionally, the BTX fraction means the C6 to C8 fractions such as benzene, toluene and xylene.

According to the first method for refining dicyclopentadiene, adoption of the above-described specific crude dicyclopentadiene as a distillation object enables to obtain high-purity refined dicyclopentadiene in a single distillation tower. Additionally, the above-described crude dicyclopentadiene can be supplied as having passed through the separation and recovery of the useful BTX fraction, and hence is advantageous from the viewpoint of the cost of the feed stock.

Additionally, the first method for refining dicyclopentadiene of the present invention enables to contribute to the effective use of the crude dicyclopentadiene that is a by-product in the production of BTX using a cracked gasoline as feed stock.

In the first method for refining dicyclopentadiene, preferably the above-described crude dicyclopentadiene contains methyldicyclopentadiene in a content of 10 to 40% by mass; and the above-described crude dicyclopentadiene is distilled in such a way that the content of methyldicyclopentadiene in the separated and recovered dicyclopentadiene is less than 1.0% by mass. It is to be noted that in the present specification, methyldicyclopentadiene (MeDCPD) means a compound represented by the following structural formula.

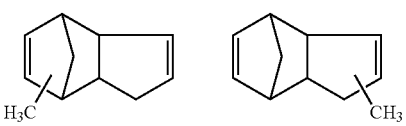

[Formula 2]

Methyldicyclopentadiene (MeDCPD)

The reaction product obtained by subjecting a cracked gasoline to a dimerization reaction contains as a by-product, a large amount of methyldicyclopentadiene; in the refinement of dicyclopentadiene, it is required to remove methyldicyclopentadiene contained in a large amount. The refined dicyclopentadiene that is obtained by the above-described refining method is capable of being particularly effective for the production of ethylidene norbornene or cycloolefin polymer.

Additionally, in the first method for refining dicyclopentadiene of the present invention, the content of dicyclopentadiene in the above-described crude dicyclopentadiene is preferably 40 to 90% by mass, and the above-described crude dicyclopentadiene is preferably distilled in such a way that the purity of the separated and recovered dicyclopentadiene is 93% by mass or more.

Further, in the first method for refining dicyclopentadiene of the present invention, the above-described crude dicyclopentadiene is preferably distilled at 130° C. or lower from the viewpoint of enhancing the recovery rate of dicyclopentadiene in relation to the crude dicyclopentadiene by suppressing the decomposition of dicyclopentadiene.

The present invention also provides a second method for refining dicyclopentadiene, wherein a dicyclopentadiene-containing fraction refined by distillation is brought into contact with an inert gas or a hydrocarbon gas having 1 to 3 carbon atoms.

According to the second method for refining dicyclopentadiene of the present invention, the hue of the dicyclopentadiene-containing fraction refined by distillation can be improved to enable to obtain dicyclopentadiene excellent in hue.

Additionally, the second method for refining dicyclopentadiene of the present invention can attain a sufficient hue improvement effect with an apparatus such as a gas-liquid contact apparatus, and hence is advantageous as compared to a method such as a method using an adsorbent or a method based on crystallization, from the viewpoint of the operation cost and the equipment cost.

In the second method for refining dicyclopentadiene of the present invention, the above-described dicyclopentadiene-containing fraction refined by distillation is preferably brought into contact with nitrogen or methane. These gases are preferable in that these gases are easily available and easy to handle in petroleum refining plants or petrochemical plants, and are low in price.

Additionally, in the second method for refining dicyclopentadiene of the present invention, the above-described dicyclopentadiene-containing fraction refined by distillation is preferably a product refined by distillation from the distillation object derived from the reaction product obtained by the dimerization reaction of a cracked gasoline. It is to be noted that in the present specification, a cracked gasoline means the C5 to C9 fractions which are by-products obtained from an ethylene cracker. On the basis of the fact that the hue of such a dicyclopentadiene-containing fraction refined by distillation can be improved, it is made possible to obtain dicyclopentadiene high in added value, in a larger amount with a satisfactory economic efficiency, from the reaction product obtained by dimerization reaction of a cracked gasoline.

Further, in the second method for refining dicyclopentadiene of the present invention, the above-described cracked gasoline is preferably the cracked gasoline by-produced in an ethylene plant that uses as feed stock a C2 fraction, a C3 fraction and a C4 fraction. Also in this case, the hue of the dicyclopentadiene-containing fraction refined by distillation can be improved, and thus it is made possible to obtain dicyclopentadiene high in added value, in a larger amount with a satisfactory economic efficiency, from the reaction product obtained by dimerization reaction of a cracked gasoline.

Additionally, in the second method for refining dicyclopentadiene of the present invention, the above-described dicyclopentadiene-containing fraction refined by distillation preferably contains dicyclopentadiene in a content of 85 to 99% by mass, and preferably contains cyclopentadiene and methylcyclopentadiene in a sum content of 0.1 to 10% by mass. According to the present invention, also from such a fraction, dicyclopentadiene from which light impurities such as cyclopentadiene and methylcyclopentadiene are sufficiently removed and which is excellent in hue can be obtained. In this case, from the remaining fraction from which higher-purity dicyclopentadiene has been extracted, useful dicyclopentadiene can be recovered efficiently, and thus it is made possible to further improve the economic efficiency in the production of dicyclopentadiene.

Additionally, in the second method for refining dicyclopentadiene of the present invention, the hue of the above-described dicyclopentadiene-containing fraction refined by distillation exceeds 100 in terms of APHA, and the hue concerned can be made to be 100 or less in terms of APHA.

Advantageous Effects of Invention

According to the present invention, high-purity dicyclopentadiene can be obtained, and additionally, a method for refining dicyclopentadiene, more advantageous than conventional methods from the viewpoint of the equipment cost and the operation cost, can be provided. Also according to the present invention, a method for refining dicyclopentadiene capable of improving the hue of the dicyclopentadiene-containing fraction refined by distillation can be provided.

DESCRIPTION OF EMBODIMENTS

Hereinafter, a preferred embodiment of the present invention is described in detail with reference to the accompanying drawings. It is to be noted that in the description of the drawings, the same symbols are used for the same components or the corresponding components, and repetitive explanations are omitted.

Figure 1:
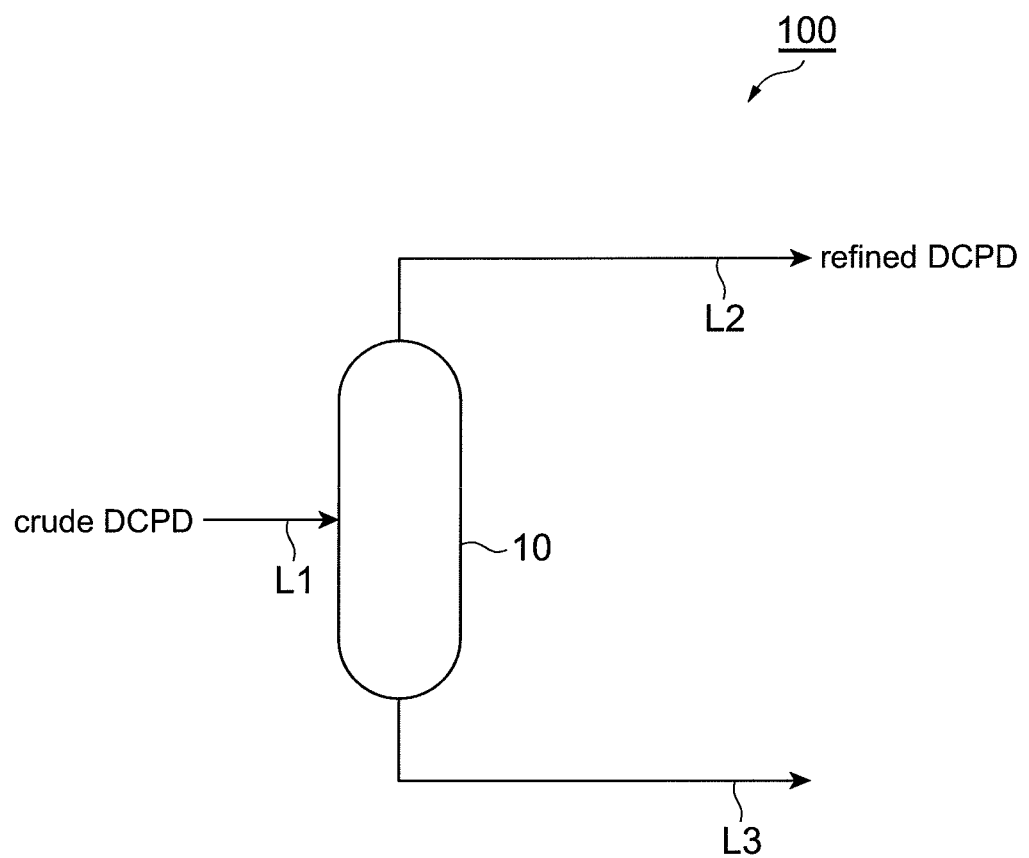
FIG. 1 is a flow chart illustrating an example of a refining apparatus of dicyclopentadiene for embodying a first method for refining dicyclopentadiene of the present invention.

FIG. 1 is a flow chart illustrating an example of a refining apparatus of dicyclopentadiene for embodying a first method for refining dicyclopentadiene of the present invention. A refining apparatus 100 illustrated in FIG. 1 is provided with a distillation tower 10 to distill a specific crude dicyclopentadiene according to the first method for refining dicyclopentadiene of the present invention. To the distillation tower 10, a recovery line L2 to recover the dicyclopentadiene separated by distillation and a recovery line L3 to take out the fraction in the tower bottom are connected.

The specific crude dicyclopentadiene according to the first method for refining dicyclopentadiene of the present invention, fed to the distillation tower 10 is a product obtained by removing a C5 fraction and a BTX fraction from the reaction product obtained by dimerization reaction of the cracked gasoline by-produced in an ethylene plant that uses as feed stock a C2 fraction, a C3 fraction and a C4 fraction. It is to be noted that an ethylene plant that uses as feed stock a C2 fraction, a C3 fraction and a C4 fraction is referred to as a LPG cracker as the case may be.

The cracked gasoline is only required to contain C5 to C9 fractions; however, for the purpose of reducing impurities similar to dicyclopentadiene, the cracked gasoline is preferably a product in which the sum of the contents of isoprene and piperylene is equal to or less than half the content of cyclopentadiene.

Additionally, as the above-described reaction product, for example, there can be used a product obtained by subjecting the above-described cracked gasoline to a dimerization reaction under the liquid phase reaction conditions in which the reaction temperature is 75° C. to 200° C.

In the present embodiment, the residual obtained by removing by distillation the unreacted C5 fraction from the above-described reaction product, and by further removing by distillation the BTX fraction, can be used as it is as the crude dicyclopentadiene according to the present invention.

The unreacted C5 fraction can be removed by a usual refinement by distillation. Additionally, the BTX fraction can be removed by a usual refinement by distillation.

Additionally, in the crude dicyclopentadiene fed to the distillation tower 10, for the purpose of making the purity of the obtained product, dicyclopentadiene, be 93% by mass or more, the sum content of isopropenylnorbornene (IPNB) and propenylnorbornene (PNB) is preferably less than 4% by mass and more preferably less than 3% by mass in a ratio in relation to dicyclopentadiene.

It is to be noted that there is a possibility that methyltetrahydroindene (MeTHI), methyldicyclopentadiene (MeDCPD) and the like are contained in the crude dicyclopentadiene in addition to isopropenylnorbornene (IPNB) and propenylnorbornene (PNB). These compounds respectively refer to the compounds represented by the following structural formulas.

TABLE 1

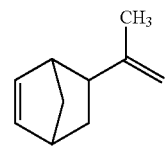

Isopropenylnorbornene (IPNB)

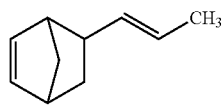

Propenylnorbornene (PNB)

TABLE 1-continued

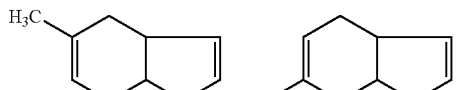

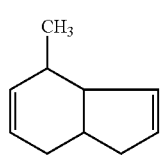

Methyltetrahydroindene (MeTHI)

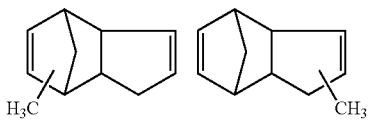

Methyldicyclopentadiene (MeDCPD)

As the distillation tower 10, a heretofore known distillation tower can be used. In the distillation tower 10, the above-described crude dicyclopentadiene can be separated, for example, into a first fraction (a fraction having a boiling points of 160 to 170° C. under normal pressure) that contains dicyclopentadiene in a high concentration, and a second fraction (a fraction having a boiling point of 172° C. or higher) that contains heavy impurities such as MeTHI and MeDCPD and is heavier than the first fraction. The first fraction is recovered through the recovery line L2 as refined dicyclopentadiene. The second fraction is recovered from the tower bottom through the recovery line L3, and can be used, for example, as a liquid fuel. Additionally, a light fraction that contains light impurities such as cyclopentadiene (CPD) and methylcyclopentadiene (MeCPD) and is lighter than the first fraction can be recovered separately, and can be used as a dicyclopentadiene recovery source or a gas fuel by preferably being made to pass through a below-described refining method.

The theoretical number of stages of the distillation tower 10 can be set at 30 to 60, and preferably at 40 to 50 from the viewpoint of the optimization of the relation between the reflux ratio and the number of distillation stages. However, the optimal number of stages is varied depending on the composition, and hence can be appropriately altered.

Additionally, the distillation in the distillation tower 10 is preferably performed at a temperature of 130° C. or lower, from the viewpoint of increasing the recovery ratio of dicyclopentadiene relative to the crude dicyclopentadiene by suppressing the decomposition of dicyclopentadiene. It is to be noted that the temperature as referred to herein means the temperature at the tower bottom.

Further, the distillation in the distillation tower 10 is preferably performed under the conditions that the pressure at the tower top is 10 to 15 kPaA, the temperature at the tower top is 90 to 105° C., and the temperature at the tower bottom is 120 to 135° C., with a reflux ratio of 4 to 8, preferably 6 to 7.

In the present embodiment, a material containing dicyclopentadiene in a content of 40 to 90% by mass is prepared as the above-described crude dicyclopentadiene, and such a crude dicyclopentadiene is preferably distilled in such a way that the first fraction contains DCPD in a content of 93% by mass or more, and more preferably 95% by mass or more.

Such distillation can be performed, for example, by controlling the reflux ratio in the distillation tower 10 or the recovery ratio of dicyclopentadiene in the distillation tower 10.

Additionally, in the case where the above-described crude dicyclopentadiene contains methyldicyclopentadiene in a content of 10 to 40% by mass, the above-described crude dicyclopentadiene is preferably distilled in such a way that the content of methyldicyclopentadiene in the above-described first fraction is less than 1.0% by mass. Such distillation can be performed, for example, by controlling the reflux ratio in the distillation tower 10 or the recovery ratio of dicyclopentadiene in the distillation tower 10.

Further, in the present embodiment, the first fraction can be taken out from the side of the distillation tower by distilling the above-described crude dicyclopentadiene under the conditions that side-cutting is performed from an optional position in the range from the tower top to the feed stage. In the sense of rendering the distillation efficient, preferably the above-described crude dicyclopentadiene is distilled under the conditions that side-cutting is performed at a position downward by 3 to 10 stages from the tower top, and the first fraction is taken out from the side of the distillation tower. In this case, the content of DCPD in the first fraction can be further improved, and at the same time, the hue of the first fraction can be made more excellent. In this case, as described above, the light fraction that is obtained from the tower top, contains light impurities such as cyclopentadiene (CPD) and methylcyclopentadiene (MeCPD) and is lighter than the first fraction can be recovered separately, and can be used as a dicyclopentadiene recovery source or a gas fuel preferably by being made to pass through a below-described refining method.

Figure 2:
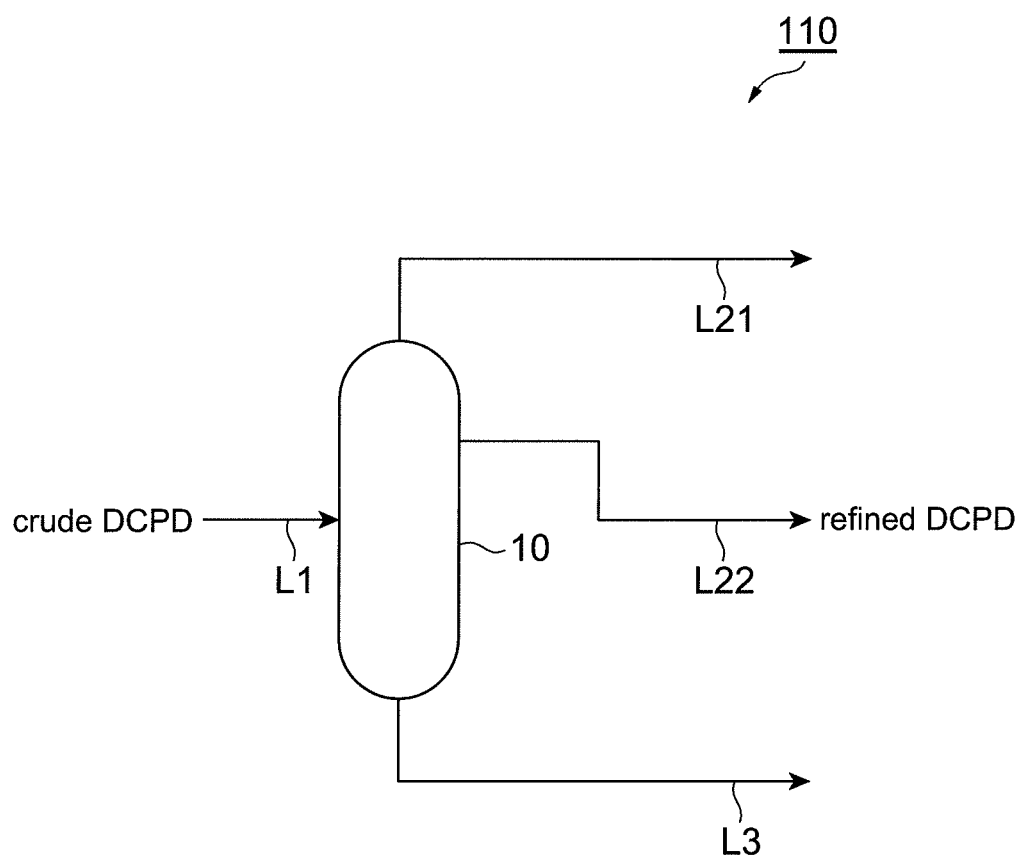
FIG. 2 is a flow chart illustrating another example of a refining apparatus of dicyclopentadiene for embodying the first method for refining dicyclopentadiene of the present invention.

FIG. 2 is a flow chart illustrating an example of a method for taking out the first fraction from the side of the distillation tower in the first method for refining dicyclopentadiene of the present invention. In the refining apparatus 110 shown in FIG. 2, L22 is a line to take out the first fraction from the side of the distillation tower 10 and L21 is a line to take out the light fraction from the tower top.

Figure 3:
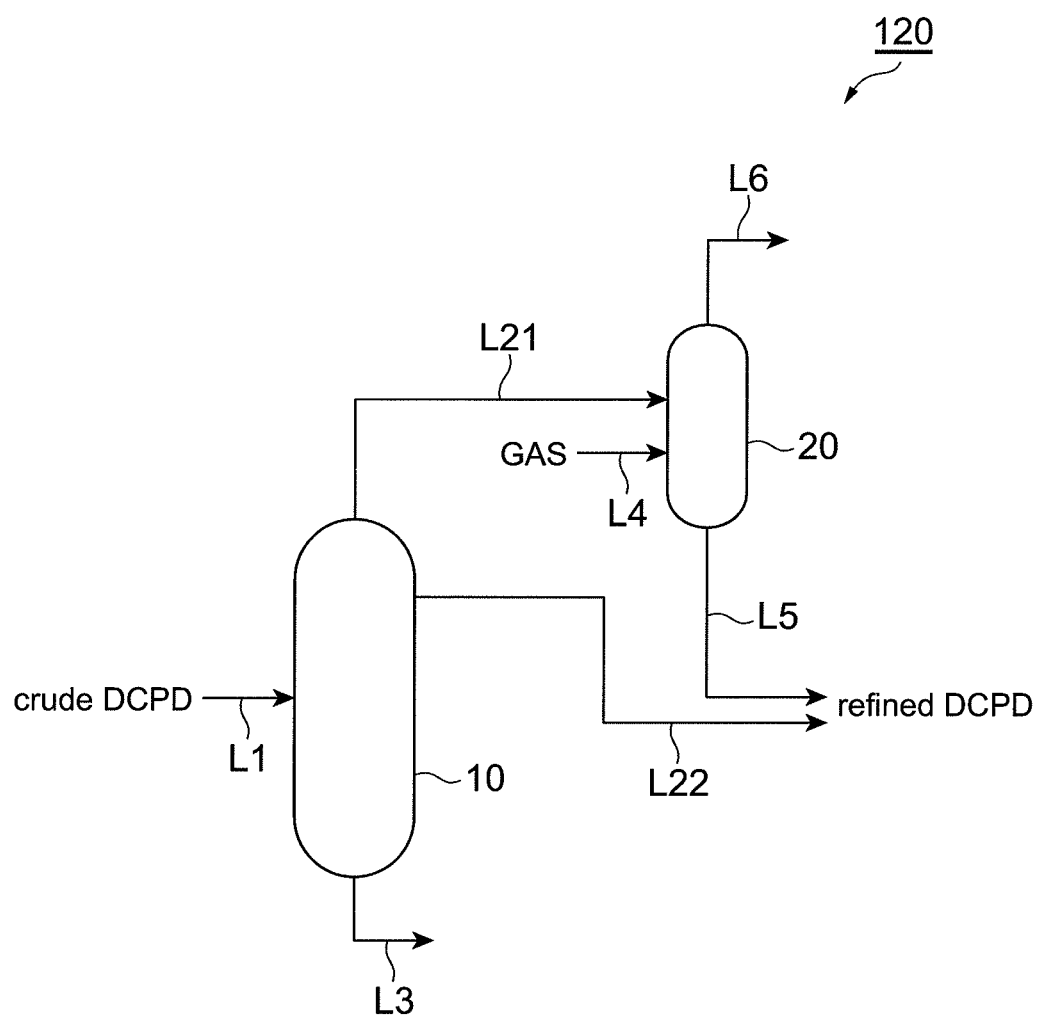
FIG. 3 is a flow chart illustrating an example of a refining apparatus of dicyclopentadiene for embodying a second method for refining dicyclopentadiene of the present invention.

FIG. 3 is a flow chart illustrating an example of a refining apparatus of dicyclopentadiene for embodying a second method for refining dicyclopentadiene of the present invention. The refining apparatus 120 shown in FIG. 3 is provided with a distillation tower 10 to distill a distillation object that contains dicyclopentadiene and a distillation tower 20 to bring the dicyclopentadiene-containing light fraction refined by distillation in the distillation tower 10 into contact with an inert gas or a hydrocarbon gas having 1 to 3 carbon atoms. To the distillation tower 10, a feed line L1 to feed to the distillation tower 10 the distillation object that contains dicyclopentadiene is connected. The distillation tower 10 and the distillation tower 20 are connected to each other with a transfer line L21, and the dicyclopentadiene-containing light fraction refined by distillation in the distillation tower 10 is fed to the distillation tower 20 through the transfer line L21. Further, connected to the distillation tower 10 is a recovery line L22 to take out the first dicyclopentadiene-containing fraction refined by distillation in the distillation tower 10. Additionally, connected to the distillation tower 20 are a feed line L4 to feed to the distillation tower 20 an inert gas or a hydrocarbon gas having 1 to 3 carbon atoms, a recovery line L5 to take out from the distillation tower 20 a dicyclopentadiene-containing liquid improved in hue and a recovery line L6 to take out the light fraction from the distillation tower 20. Thus, in the distillation tower 20, the second method for refining dicyclopentadiene of the present invention is embodied.

As the dicyclopentadiene-containing distillation object fed from L1, there can be used a product derived from the reaction product obtained by dimerization reaction of a cracked gasoline, or a dicyclopentadiene-containing liquid that contains as impurities lighter fractions than dicyclopentadiene such as cyclopentadiene or methylcyclopentadiene.

From the viewpoint that high-purity dicyclopentadiene is efficiently obtained by a single distillation from the recovery line L22, the distillation object is preferably a product derived from the reaction product based on the dimerization reaction of a cracked gasoline. It is to be noted that the cracked gasoline as referred to herein means the C5 to C9 fractions that are by-products in an ethylene cracker. Also from the same viewpoint, the cracked gasoline is preferably a product obtained from a LPG cracker. It is also to be noted that a LPG cracker means an ethylene cracker that uses as feed stock a C2 fraction, a C3 fraction and a C4 fraction.

Further, in the present embodiment, preferably fed as the above-described distillation object to the distillation tower 10 is a product obtained by removing the unreacted C5 fraction and the unreacted BTX fraction from the reaction product obtained by dimerization reaction of the cracked gasoline obtained from a LPG cracker. The unreacted C5 fraction and the unreacted BTX fraction can be respectively removed by a usual refinement by distillation.

In the above-described distillation object, the sum content of isopropenylnorbornene (IPNB) and propenylnorbornene (PNB) is preferably a proportion of 4% by mass or less in relation to dicyclopentadiene.

It is to be noted that there is a possibility that methyltetrahydroindene (MeTHI), methyldicyclopentadiene (MeDCPD) and the like are contained in the above-described distillation object derived from the reaction product, in addition to isopropenylnorbornene (IPNB) and propenylnorbornene (PNB). These compounds respectively refer to the compounds represented by the above-described structural formulas in Table 1.

As the distillation tower 10, a heretofore known distillation tower can be used. In the distillation tower 10, the above-described distillation object is separated, for example, into the light fraction that contains light impurities such as cyclopentadiene (CPD) and methylcyclopentadiene (MeCPD) and contains dicyclopentadiene, the first fraction that contains dicyclopentadiene in a high concentration and the second fraction (a fraction having a boiling point of 172° C. or higher) that contains heavy impurities such as MeTHI and MeDCPD. The light fraction that contains light impurities such as CPD and MeCPD and contains dicyclopentadiene is transferred to the distillation tower 20 through the transfer line L21, and the first fraction that contains dicyclopentadiene in a high concentration is recovered as a product through the recovery line L22.

The theoretical number of stages of the distillation tower 10 can be set at 30 to 60, and preferably at 40 to 50 from the viewpoint of the optimization of the relation between the reflux ratio and the number of distillation stages. However, the optimal number of stages is varied depending on the composition, and hence can be appropriately altered. Additionally, the distillation in the distillation tower 10 is preferably performed under the conditions that the pressure at the tower top is 10 to 15 kPaA, the temperature at the tower top is 90 to 105° C., and the temperature at the tower bottom is 120 to 135° C., with a reflux ratio of 4 to 8, preferably 6 to 7.

In the present embodiment, the above-described distillation object is distilled in such a way that the light fraction contains DCPD preferably in a content of 80 to 99% by mass and more preferably in a content of 85 to 95% by mass.

Additionally, in the present embodiment, the first fraction is taken out from the side of the distillation tower by distilling the above-described distillation object under the conditions that side-cutting is performed from an optional position in the range from the tower top to the feed stage. In the sense of rendering the distillation efficient, preferably the above-described distillation object is distilled under the conditions that side-cutting is performed at a position downward by 3 to 10 stages from the tower top, and the first fraction is taken out from the side of the distillation tower. In this case, it is preferable to perform the distillation in such a way that the content of dicyclopentadiene in the first fraction that contains dicyclopentadiene in a high concentration is 93% by mass or more and the content of MeDCPD is less than 1.0% by mass. Additionally, it is preferable to refine, in the distillation tower 20, the light fraction that is obtained from the tower top under the above-described conditions and contains light impurities such as CPD and MeCPD and contains dicyclopentadiene. In this case, the hue of the first fraction obtained as a high-purity DCPD product can be made more excellent, and at the same time, from the light fraction, DCPD improved in hue by the second refining method of the present invention can be sufficiently obtained.

When distillation is performed with reference to the hue of the light fraction, the hue of the light fraction usually exceeds 100 in terms of APHA; however, the hue of the light fraction may be 200 or more. It is to be noted that APHA is measured by the color measurement method specified in ASTM D1209. Also in this case, the hue of the first fraction obtained as a high-purity DCPD product can be made more excellent, and at the same time, from the light fraction, DCPD improved in hue by the second refining method of the present invention can be sufficiently obtained.

In the distillation tower 20, the second method for refining dicyclopentadiene of the present invention is embodied. In the present embodiment, a distillation tower that is a packed tower is used; however, a vessel that permits gas-liquid contact and permits taking-out of a predetermined liquid can be used without any limitation. Examples of such a vessel include a distillation tower that is a tray tower.

The theoretical number of stages of the distillation tower 20 is preferably set at 10 to 30, and more preferably at 15 to 25 from the viewpoint of efficient separation. However, the optimal number of stages is varied depending on the composition, and hence can be appropriately altered. In the present embodiment, the light fraction can be fed from the tower top of the distillation tower 20 and an inert gas or a hydrocarbon gas having 1 to 3 carbon atoms can be fed from the tower bottom of the distillation tower 20.

As the inert gas, nitrogen, argon or carbon dioxide can be used. As the hydrocarbon gas having 1 to 3 carbon atoms, methane, ethane or propane can be used. In the present embodiment, because of easy availability or easy handleability, nitrogen, methane or ethane is preferable, and nitrogen or methane is more preferable.

The contact of the light fraction with the inert gas or the hydrocarbon gas having 1 to 3 carbon atoms can be performed at normal temperature under normal pressure; for the purpose of more efficiently removing light impurities such as CPD and MeCPD, preferably the light fraction is preheated at 60 to 90° C., and then fed to the distillation tower 20.

The flow rate of the light fraction and the flow rate of the inert gas or the hydrocarbon gas having 1 to 3 carbon atoms into the distillation tower 20 are preferably set in such a way that the volume ratio of the above-described gas to the light fraction is 50 to 200.

By passing through the above-described gas-liquid contact step, from the distillation tower 20, a dicyclopentadiene-containing liquid that is improved in hue and contains a high-purity dicyclopentadiene is recovered through the recovery line L5. In the present embodiment, the hue of the dicyclopentadiene-containing liquid is preferably 100 or less in terms of APHA, and more preferably 60 or less in terms of APHA.

Figure 4:
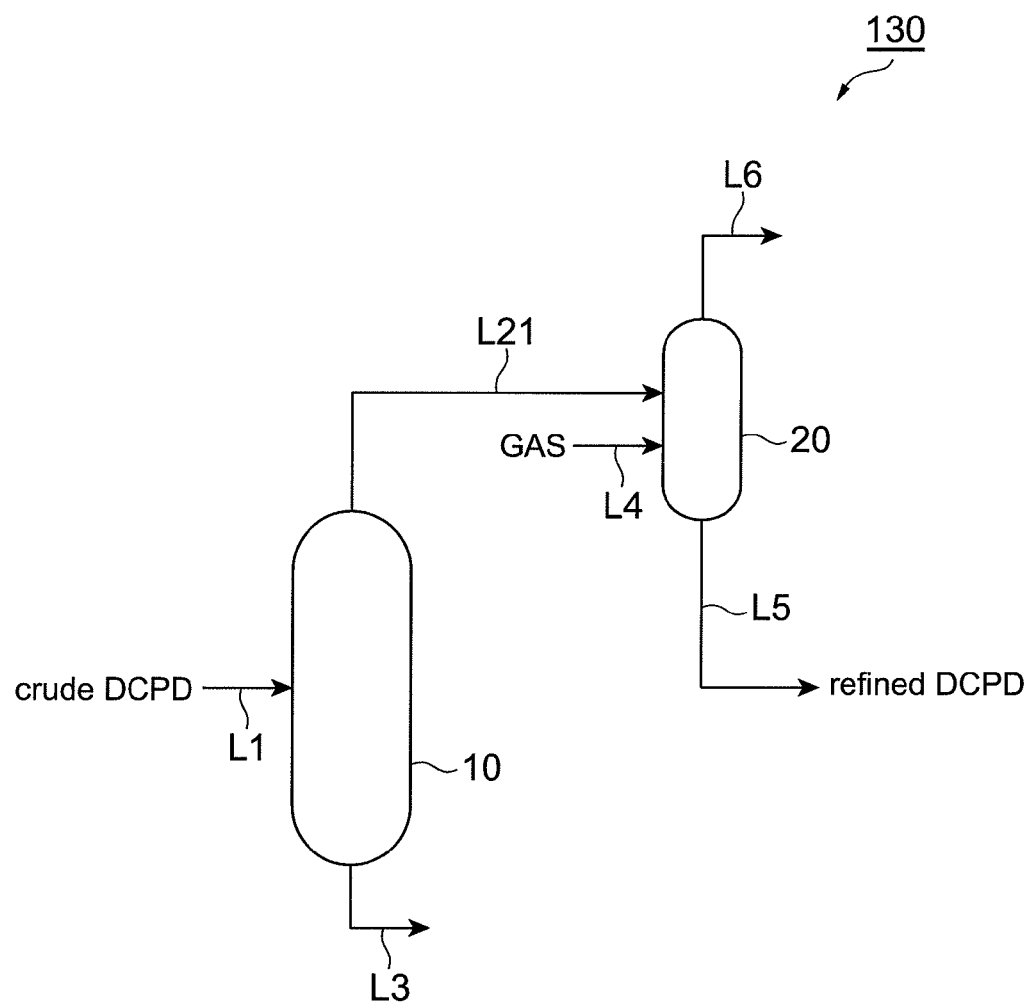
FIG. 4 is a flow chart illustrating another example of a refining apparatus of dicyclopentadiene for embodying the second method for refining dicyclopentadiene of the present invention.

FIG. 4 is a flow chart illustrating another example of a refining apparatus of dicyclopentadiene for embodying the second method for refining dicyclopentadiene of the present invention. The refining apparatus 130 of dicyclopentadiene shown in FIG. 4 has the same configuration as the refining apparatus 120 of dicyclopentadiene except that the refining apparatus 130 of dicyclopentadiene shown in FIG. 4 is not provided with the recovery line L22 in the refining apparatus 120 of dicyclopentadiene.

In the present embodiment, the fraction that has been refined by distillation in the distillation tower 10 and contains dicyclopentadiene is refined in the distillation tower 20 by the second method for refining dicyclopentadiene of the present invention.

Also in the refining apparatus 130 of dicyclopentadiene, the refinement of dicyclopentadiene can be performed under the same conditions as in the refining apparatus 120 of dicyclopentadiene except that the taking-out of the first fraction is omitted.

The distillation in the distillation tower 10 is preferably performed under the conditions that the pressure at the tower top is 10 to 15 kPaA, the temperature at the tower top is 90 to 105° C., and the temperature at the tower bottom is 120 to 135° C., with a reflux ratio of 4 to 8, preferably 6 to 7.

In the present embodiment, the above-described distillation object fed through L1 is distilled in such a way that the above-described fraction that is taken out from L21 and contains dicyclopentadiene contains DCPD preferably in a content of 80 to 99% by mass, and more preferably in a content of 85 to 95% by mass. In this case, a DCPD product that is high in purity and excellent in hue can be efficiently obtained by the refinement and the refinement by distillation in the distillation tower 20, according to the second refining method of the present invention.

Additionally, the hue of the dicyclopentadiene-containing fraction taken out from the above-described L21 usually exceeds 100 in terms of APHA; however, the hue of the concerned fraction may be 200 or more. Also in this case, a DCPD product that is high in purity and excellent in hue can be efficiently obtained by the refinement and the refinement by distillation in the distillation tower 20, according to the second refining method of the present invention.

The preferred embodiment of the present invention has been described above in detail; however, the present invention is not limited to the above-described embodiment, and may be replaced with other embodiments. For example, in another embodiment, the refining method may be altered to a method in which the purity of dicyclopentadiene is stepwise enhanced by twice performing the distillation, instead of increasing the theoretical number of stages or the reflux ratio in the distillation tower 10.

According to the method for refining dicyclopentadiene of the present invention, by preparing a specific crude dicyclopentadiene, a high-purity dicyclopentadiene can be obtained by performing a single distillation with common distillation equipment. Additionally, the present invention can provide an industrially advantageous method for producing dicyclopentadiene in which method a high-purity dicyclopentadiene is obtained from LPG. In other words, the concerned method for producing dicyclopentadiene includes: a first step of preparing the cracked gasoline by-produced in an ethylene plant that uses as feed stock a C2 fraction, a C3 fraction and a C4 fraction; a second step of subjecting the cracked gasoline prepared in the first step to a dimerization reaction; a third step of obtaining a crude dicyclopentadiene by removing a C5 fraction and a BTX fraction from the reaction product obtained in the second step; and a fourth step of separating and recovering dicyclopentadiene by distilling the crude dicyclopentadiene obtained in the third step. The second to fourth steps can be performed under the above-described conditions.

Additionally, the method for refining dicyclopentadiene according to the present invention which method includes a step of bringing the dicyclopentadiene-containing fraction that is refined by distillation into contact with an inert gas or a hydrocarbon gas having 1 to 3 carbon atoms can be used, for example, as a method for improving the hue of the dicyclopentadiene-containing fraction colored due to a trace amount of light impurities or a method for removing light impurities from a dicyclopentadiene-containing fraction in which the separation and the removal of light impurities are incomplete.

EXAMPLES

Hereinafter, the present invention is described in detail with reference to Examples, but the present invention is not limited by these Examples.

Example 1

A crude dicyclopentadiene having the composition shown in Table 2 was prepared, wherein the crude dicyclopentadiene was obtained by removing a C5 fraction and a BTX fraction from the reaction product obtained by dimerization reaction of the cracked gasoline by-produced in a LPG cracker.

To a distillation tower (having a theoretical number of stages of 40) of a refining apparatus having the same configuration as the configuration of the refining apparatus 100 shown in FIG. 1, the above-described crude dicyclopentadiene preheated to 80° C. was fed at a flow rate of 40 g/min, and the pressure and the reflux ratio at the tower top were set at 12.5 kPaA and 8, respectively. The flow rate of a first fraction recovered from the tower top was 25 g/min and the hue of this fraction was 200+ in terms of APHA. Additionally, a second fraction was recovered from the tower bottom at a flow rate of 15 g/min. In this case, the tower top temperature was 99° C. and the tower bottom temperature was 118° C.

The compositions of the obtained first and second fractions are shown in Table 2. The composition analysis was performed with a gas chromatograph.

TABLE 2

|  | Fed crude dicyclopentadiene | First fraction | Second fraction |
| --- | --- | --- | --- |
| CPD (% by mass) | 0.1 | 0.3 | 0.0 |
| MeCPD (% by mass) | 0.0 | 0.1 | 0.0 |
| IPNB and PNB (% by mass) | 2.5 | 3.9 | 0.00 |
| DCPD (% by mass) | 72.4 | 95.0 | 37.0 |
| MeTHI (% by mass) | 2.7 | 0.7 | 5.7 |
| MeDCPD (% by mass) | 16.3 | 0.00 | 40.2 |
| Others (heavy fraction) (% by mass) | 4.3 | 0.0 | 13.8 |

Example 2

To a distillation tower (having a theoretical number of stages of 20) of a refining apparatus having the same configuration as the configuration of the refining apparatus 110 shown in FIG. 2, the above-described crude dicyclopentadiene preheated to 80° C. was fed at a flow rate of 100 g/min, and the pressure and the reflux ratio at the tower top were set at 12.5 kPaA and 40, respectively. A first fraction was taken out by side-cutting at a position of the fifth stage from the tower top, and was recovered at a flow rate of 66 g/min. The recovery flow rate of a light fraction from the tower top was 8 g/min, and a second fraction was recovered from the tower bottom at a flow rate of 26 g/min. In this case, the tower top temperature was 103° C., and the tower bottom temperature was 124° C. The content of dicyclopentadiene in the first fraction was found to be 93.3% by mass, and the hue of the first fraction was 60 in terms of APHA.

Example 3

A dicyclopentadiene-containing fraction having a composition shown in Table 3 was prepared, wherein the dicyclopentadiene-containing fraction was obtained by refinement by distillation from a fraction obtained by removing a C5 fraction and a BTX fraction from the reaction product obtained by dimerization reaction of the cracked gasoline by-produced in a LPG cracker. The hue of this dicyclopentadiene-containing fraction was 200+ in terms of APHA.

To a distillation tower having a theoretical number of stages of 10, the above-described dicyclopentadiene-containing fraction preheated to 65° C. was fed from the tower top at a flow rate of 200 ml/min, nitrogen was fed from the tower bottom at a flow rate of 2.6 L/h, and thus a gas-liquid contact was performed. Thus, a recovered fraction was obtained at a flow rate of 198 ml/min. The hue of this recovered fraction was about 50 in terms of APHA. Additionally, it was verified that in the recovered fraction, as shown in Table 3, the contents of CPD and MeCPD were reduced while the content of DCPD was being sufficiently maintained. The composition analysis was performed with a gas chromatograph.

TABLE 3

|  | Fed dicyclopentadiene-containing fraction | Recovered fraction |
| --- | --- | --- |
| CPD (% by mass) | 0.16 | 0.01 |
| MeCPD (% by mass) | 0.12 | 0.00 |
| IPNB (% by mass) | 2.07 | 2.17 |
| PNB (% by mass) | 1.14 | 1.20 |
| DCPD (% by mass) | 94.77 | 94.60 |
| MeTHI (% by mass) | 0.32 | 0.78 |
| MeDCPD (% by mass) | 1.37 | 1.24 |
| Others (% by mass) | 0.05 | 0.00 |
| Hue (APHA) | 200+ | About 50 |

Example 4

A dicyclopentadiene-containing fraction having the composition shown in Table 4 was prepared by distillation from the same distillation object as in Example 3. The hue of this dicyclopentadiene-containing fraction was 200+ in terms of APHA.

To a distillation tower having a theoretical number of stages of 20, the above-described dicyclopentadiene-containing fraction preheated to 90° C. was fed from the tower top at a flow rate of 310 L/h, methane was fed from the tower bottom at a flow rate of 35 kg/h, and thus a gas-liquid contact was performed. Thus, a recovered fraction was obtained at a flow rate of 300 L/h. The hue of this recovered fraction was 50 in terms of APHA. Additionally, it was verified that in the recovered fraction, as shown in Table 4, the content of DCPD was large, and the contents of CPD and MeCPD were reduced.

TABLE 4

|  | Fed dicyclopentadiene-containing fraction | Recovered fraction |
| --- | --- | --- |
| CPD (% by mass) | 1.0 | 0.0 |
| MeCPD (% by mass) | 1.7 | 0.02 |
| IPNB and PNB (% by mass) | 4.2 | 4.3 |
| DCPD (% by mass) | 93.0 | 95.5 |
| Others (% by mass) | 0.1 | 0.1 |
| Hue (APHA) | 200+ | 50 |

DESCRIPTION OF SYMBOLS

10 . . . Distillation tower; 20 . . . Distillation tower; 100, 110, 120, 130 . . . Refining apparatus of dicyclopentadiene

The invention claimed is:

1. A method for distilling dicyclopentadiene consisting essentially of:
   distilling a crude dicyclopentadiene, which comprises 10 to 40% by mass methyl dicyclopentadiene, once to obtain at least a first fraction comprising a separated and recovered dicyclopentadiene, which comprises less than 1.0% by mass methyl dicyclopentadiene, and a second fraction that is heavier than the first fraction
   wherein the crude dicyclopentadiene is obtained by removing a C5 fraction and a BTX fraction from a reaction product obtained by performing a dimerization reaction on a cracked gasoline by-produced in an ethylene plant that uses as a feedstock a C2 fraction, a C3 fraction and a C4 fraction.

2. The method for distilling dicyclopentadiene according to claim 1, wherein:
   the content of dicyclopentadiene in the crude dicyclopentadiene is 40 to 90% by mass; and
   the crude dicyclopentadiene is distilled in such a way that the purity of the separated and recovered dicyclopentadiene is 93% by mass or more.

3. The method for distilling dicyclopentadiene according to claim 1, wherein the crude dicyclopentadiene is distilled at 130° C. or lower.

4. The method for distilling dicyclopentadiene according to claim 1, wherein the crude dicyclopentadiene is distilled over 30 to 60 stages of the theoretical number of stages.

5. The method for distilling dicyclopentadiene according to claim 2, wherein the crude dicyclopentadiene is distilled at 130° C. or lower.

6. The method for distilling dicyclopentadiene according to claim 2, wherein the crude dicyclopentadiene is distilled over 30 to 60 stages of the theoretical number of stages.

7. The method for distilling dicyclopentadiene according to claim 3, wherein the crude dicyclopentadiene is distilled over 30 to 60 stages of the theoretical number of stages.

8. The method for distilling dicyclopentadiene according to claim 2, wherein the crude dicyclopentadiene is distilled at 130° C. or lower and over 30 to 60 stages of the theoretical number of stages.

9. The method for distilling dicyclopentadiene according to claim 1, wherein the cracked gasoline by-product by-produced in an ethylene plant that uses as a feedstock a C2 fraction, a C3 fraction and a C4 fraction comprises isoprene and piperylene and the sum of these two components is half or less than half of an amount of cyclopentadiene contained in the by-product.

10. The method for distilling dicyclopentadiene according to claim 1, wherein the reaction product is obtained by performing the dimerization reaction under liquid-phase reaction conditions at a temperature of from 75° C. to 200° C.

11. The method for distilling dicyclopentadiene according to claim 1, wherein the sum content of isopropenylnorbornene and propenylnorborene in the crude dicyclopentadiene is less than 4% by mass in relation to dicyclopentadiene content.

* * * * *